United States Patent [19]

Borzone

[11] 4,278,091
[45] Jul. 14, 1981

[54] SOFT TISSUE RETAINER FOR USE WITH BONE IMPLANTS, ESPECIALLY BONE STAPLES

[75] Inventor: Rocco R. Borzone, Emerson, N.J.

[73] Assignee: Howmedica, Inc., New York, N.Y.

[21] Appl. No.: 117,685

[22] Filed: Feb. 1, 1980

[51] Int. Cl.³ .................... A61B 17/04; A61B 17/08
[52] U.S. Cl. ............................ 128/334 C; 128/92 B;
  128/337; 411/469; 411/471; 411/475
[58] Field of Search ............... 128/334 C, 334 R, 335,
  128/337, 92 B, 92 D, 92 BA, 92 BB; 85/49, 13, 29

[56] References Cited

U.S. PATENT DOCUMENTS

| 2,472,009 | 5/1949 | Gardner | 128/335 |
|---|---|---|---|
| 2,919,621 | 1/1960 | Langdon | 85/29 |
| 2,952,254 | 9/1960 | Keating | 128/92 BB |
| 3,855,638 | 12/1974 | Pilliar | 128/334 R X |
| 3,951,138 | 4/1976 | Akopov | 128/337 X |
| 3,973,277 | 8/1976 | Semple et al. | 3/1 |
| 4,047,524 | 9/1977 | Hall | 128/92 B X |
| 4,187,558 | 2/1980 | Dahlen et al. | 3/1 |

FOREIGN PATENT DOCUMENTS 1558965  1/1980  United Kingdom .................. 128/92 B

OTHER PUBLICATIONS

Product Release-Richards Fixation Staples, Richards Manufacturing Co., Inc., 1978.
DePalma Staple, Howmedica, Inc.-Orthopaedics Division, 1978 Catalog, p. D-107.
"Porous Surfaced Vitallium Staples", Pilliar et al., South African Journal of Surgery, vol. 10, No. 2, Jun. 1972, pp. 63-70.
"The Fixation Staple with Bite from Richards", Journal of Bone & Joint Surgery, Mar. 1980, p. 9.

Primary Examiner—Ronald L. Frinks
Attorney, Agent, or Firm—Francis X. Murphy; Charles J. Knuth; Lawrence C. Akers

[57] ABSTRACT

A novel combination of a bone implant, e.g. a bone staple, and a tissue retention element in sliding relation therewith is disclosed. The tissue retention element is provided with a multiplicity of teeth capable of piercing and holding in place adjacent soft tissue when the implant is driven into the bone structure of a patient. Since the tissue retention element is separable from the implant, the same element can be used in combination with different bone implants.

12 Claims, 4 Drawing Figures

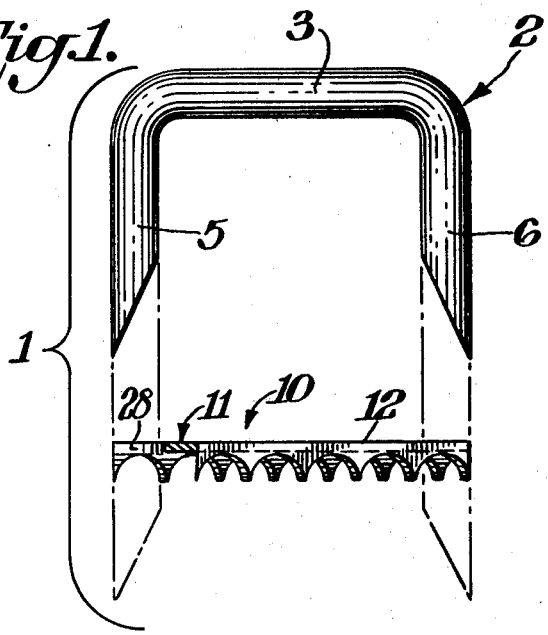
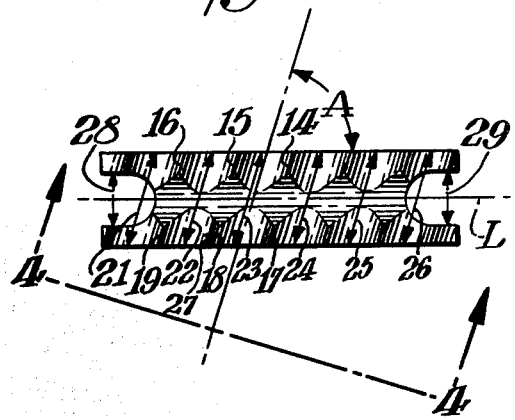
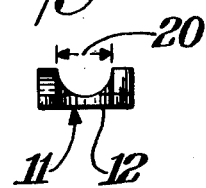
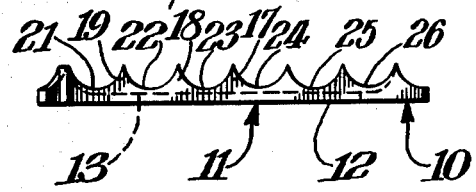

SOFT TISSUE RETAINER FOR USE WITH BONE IMPLANTS, ESPECIALLY BONE STAPLES

BACKGROUND OF THE INVENTION

It often becomes necessary in the surgical arts to reapply soft tissue (e.g., ligaments, muscle, cartilage and tendons) to the bone structure of a patient so as to cause adherence and growth of the soft tissue to the bone. Thus, for example, soft tissue torn loose from the underlying bone in an injury is so rejoined. In other operations, soft tissue is surgically separated from the underlying bone so that it can be shortened or moved, and is then rejoined to the bone. An example of such an operation is the well known surgical procedure in which the patellar tendon is translated medially to inhibit lateral subluxation of the patella in the femoral groove.

Surgical staples provided with soft tissue retaining teeth on the underside of the transverse bridge member are known. An example of such a staple is the Richards Fixation Staple (Richards Manufacturing Co., Inc.; Memphis, Tenn.). Since the orthopedic surgeon will usually have need for other staples not having such soft tissue retaining teeth, he will have to maintain a double inventory of staples. Additionally, depending on the particular problem with which he is faced, the surgeon may wish to employ a soft tissue retention capability in combination with the particular characteristics of a certain type of bone staple (e.g., compression staple, non-compression staple, barbed staple, non-barbed staple, etc.). Such freedom of combination is not provided by commercial products in which the soft tissue retaining teeth are integral with and not separable from the remainder of the staple.

U.S. Pat. No. 3,855,638 discloses a staple for the rejoining of soft tissue to bone wherein a portion of the staple is provided with a porous coating capable of sustaining soft tissue ingrowth. This coating, formed by sintering metal particles onto the surface of the staple, provides some soft tissue retention by friction immediately after implantation but does not pierce the soft tissue. Thus, the possibility that the soft tissue may slip relative to the staple and bone before substantial soft tissue ingrowth occurs is not precluded.

SUMMARY OF THE INVENTION

It is an object of the present invention to provide a versatile system allowing a physician to add a soft tissue retention capability when desired to his preexisting stock of bone staples without having to maintain a double inventory of staples (i.e., staples with and without soft tissue retention capability). It is also an object of the invention to provide a bone staple and tissue retention element combination designed to grip soft tissue and hold it in place upon the bone structure of a patient until it readheres fully, thereby substantially eliminating the possibility of slippage of the soft tissue relative to the bone after implantation of the combination.

These and other objects of the invention are achieved with a novel combination of (1) a bone staple comprising a transverse portion and a plurality of legs integral with said transverse portion, said legs being substantially parallel, and (2) a tissue retention element separable from said staple and comprising a base having an upper face and a lower face, means receiving said legs so that said retention element can slide upon said legs to a limiting position in which said upper face abuts said transverse portion, and a multiplicity of teeth distributed upon and extending from said lower face, said teeth being capable of piercing adjacent soft tissue when said staple is driven into the bone structure of a patient, whereby said retention element holds said soft tissue in place relative to said bone structure.

In a preferred embodiment of the novel combination, the teeth are distributed upon the lower face of said base in a plurality of parallel rows and have faces defining a series of parallel grooves, which grooves intersect said rows of teeth in a non-perpendicular fashion. The teeth in adjacent rows are staggered, i.e. non-aligned laterally, when viewed in planes parallel to the rows of teeth. This preferred embodiment may be oriented in use so that the parallel rows of teeth are substantially perpendicular to the longitudinal axis of a piece of collagenous soft tissue (e.g., a ligament) sought to be rejoined to bone. As the staple is driven fully into the bone, the teeth of the tissue retention element pierce the soft tissue and split it into strands. These strands are received and held firmly in place upon the bone by the above-described series of grooves, parallel to each other but angled with respect to the longitudinal axis of the piece of soft tissue. This configuration of staggered teeth and grooves provides excellent resistance to displacement of the soft tissue relative to the bone staple-retention element combination, in particular, displacement of the soft tissue along its longitudinal axis. As broadly conceived, the present invention also includes a unitary bone staple provided on the lower face of its transverse portion with the preferred pattern of teeth and grooves described immediately above.

DETAILED DESCRIPTION OF THE INVENTION

The invention will be described in detail with reference to a preferred embodiment thereof, which is a separable combination of a bone staple and a tissue retention element. Reference to this embodiment does not limit the scope of the invention, which is limited only by the scope of the claims. In the drawings:

FIG. 1 is an exploded front view of a bone staple-tissue retention element combination of the invention, with a portion of the tissue retention element broken away to show the means receiving one of the legs of the staple;

FIG. 2 is a bottom view of the tissue retention element of the combination of FIG. 1;

FIG. 3 is an inverted end view of the tissue retention element shown in FIG. 1; and FIG. 4 is a view along line 4—4 of FIG. 2.

A preferred embodiment of the invention, i.e. a bone staple-tissue retention element combination 1, is shown in FIG. 1. Staple 2 is a compression staple comprising a transverse arm 3 and a pair of legs 5 and 6 integral with and perpendicular to arm 3. Such a staple is well known in the surgical arts and is not by itself inventive. A wide variety of other compression staples, such as the barbed staple disclosed in U.K. Pat. No. 1,558,965, and non-compression staples may also be employed in the present invention. The bone staple may also be a table staple, in which the transverse portion of the staple is a plate, rather than an arm, having two or more legs parallel to one another. In fact the invention is broadly conceived to include the use of a staple in which the transverse portion is not perpendicular to the legs of the staple, e.g., an angle staple, or the use of a bone implant having only a single leg such as a headed bone nail or screw. In the latter case, the single leg of the implant may be slidingly received by a hole in the tissue retention element.

Tissue retention element 10 and bone staple 2 are preferably both made of metal, e.g. stainless steel or cobalt-chromium-molybdenum surgical implant alloy. Element 10 may also be made of any other rigid structural material, such as reinforced carbon or a strong and rigid ceramic or plastic material. Tissue retention element 10 is completely separable from bone staple 2, as shown in FIG. 1. Element 10 comprises a rectangular base 11 having an upper face 12 and a parallel lower face including bottom line 13 (see FIG. 4), and a multiplicity of teeth, e.g. 14 to 19, distributed upon and extending from the lower face. A wide variety of tooth shapes may be employed, as long as the teeth are capable of piercing soft tissue when the legs of the staple are driven into the bone structure of a patient with the tissue retention element in position between said legs. One preferred tooth shape is the triangular prism. Element 10 can slide upon legs 5 and 6 to a limiting position in which upper face 12 abuts arm 3, with legs 5 and 6 being loosely received within slots 28 and 29 in base 11.

As can be seen in FIGS. 2 and 3, teeth 14 to 19 etc., are distributed in two rows, both parallel to center line L bisecting rectangular base 11. When viewed in the frontal plane of FIG. 1, which is parallel to the plane formed by arm 3 and legs 5 and 6, the teeth in the two rows appear in a staggered relationship. The teeth are preferably formed by milling a piece of metal stock having the length and width shown in FIG. 2 of element 10 and a height greater than or equal to that shown in FIG. 3. Circular lengthwise horizontal groove 20 is first cut into the piece of metal, followed by a series of circular horizontal grooves 21 to 26 oriented at an acute angle A with respect to center line L. Finally, slots 28 and 29 are milled out. Groove 20 may be cut slightly deeper than grooves 21 to 26 as shown in the figures (bottom line 13 of groove 20 is shown in FIG. 4), thereby rendering grooves 21 to 26 discontinuous near the center line L, but this is not a necessary feature of the invention. Tissue retention element 10 may also be made by any other means known in the art, e.g. by casting.

The pattern of teeth and grooves shown in FIGS. 1 to 4 results from the milling operation described above. Side faces of teeth 15, 16, 18 and 19 define groove 22, as can be seen in FIGS. 2 and 4. Similarly, side faces of other combinations of four teeth define grooves 21 and 23 to 26. Grooves 21 to 26 are oriented at an acute angle A relative to center line L and thus also to the two parallel rows of teeth. FIG. 4 is a view of element 10 in a plane rotated by 90°-A from the frontal plane of FIG. 1. In this rotated plane the teeth in the two parallel rows appear in an aligned relationship. The free ends of the teeth, e.g. tooth 18, have approximately the shape of triangular prisms although three of the four faces extending from the apex edge, e.g. line 27, are curved rather than flat.

The novel combination 1 is used in the following manner. A piece of soft tissue (e.g., tendon, ligament, muscle, cartilage) is held at the desired location on the bone to which it is to be rejoined. Combination 1 is then placed over the piece of soft tissue, with arm 3 substantially perpendicular to the lengthwise axis of the soft tissue and legs 5 and 6 within slots 28 and 29. The legs 5 and 6 of staple 2 are then driven fully into the bone of the patient, thereby causing teeth 14 to 19, etc., to pierce the soft tissue. It is not necessary or desired to drive the teeth themselves deeply into the patient's bone, although they may come into contact with the outer surface of the bone without causing any harm to the bone structure. The tissue retention element 10 grips the soft tissue and holds it firmly in the desired location upon the patient's bone by means of the piercing action of the teeth and the compressive action of element 10. The complex pattern of teeth and grooves provides a series of tortuous paths for the soft tissue. Thus, with reference to FIG. 2, the lengthwise axis of the piece of soft tissue will be substantially perpendicular to line L. Teeth 17 and 18, for example, will split the soft tissue to force a strand thereof through that portion of angled groove 23 below line L in FIG. 2. Tooth 15, however, will further split the strand so that a part of it is forced through that portion of angled groove 22 above line L in FIG. 2 while the rest remains in angled groove 23 above line L. This splitting and resplitting action is repeated along the length of tissue retention element 10. The piece of soft tissue is thus held securely against all modes of displacement relative to combination 1, in particular slippage along the lengthwise axis of the piece of soft tissue, as soon as legs 5 and 6 have been fully driven into the bone. No substantial tissue ingrowth into the structure of combination 1 will occur, thus facilitating removal of the combination when desired.

I claim:
1. In combination
   a bone staple comprising a transverse portion and a plurality of legs integral with said transverse portion, said legs being substantially parallel, and
   a tissue retention element separable from said staple and comprising a base having an upper face and a lower face, means receiving said legs so that said retention element can slide upon said legs to a limiting position in which said upper face abuts said transverse portion, and a multiplicity of teeth distributed upon and extending from said lower face, said teeth being capable of piercing adjacent soft tissue when said staple is driven into the bone structure of a patient, whereby said retention element holds said soft tissue in place relative to said bone structure.

2. The combination of claim 1 wherein said legs are substantially perpendicular to said transverse portion.

3. The combination of claim 2 wherein said teeth are distributed upon said lower face in a plurality of parallel rows.

4. The combination of claim 3 wherein the teeth in adjacent parallel rows are laterally staggered when viewed in planes parallel to said rows.

5. The combination of claim 4 wherein said teeth have faces defining a series of parallel grooves oriented so as to intersect said rows in a non-perpendicular fashion.

6. The combination of claim 5 wherein the cross-sections of said parallel grooves are concave curves.

7. The combination of claim 6 wherein said cross-sections are circular arcs.

8. The combination of claim 3, 4 or 5 wherein said teeth are triangular prisms.

9. The combination of claim 1 wherein said legs are slidingly received within a plurality of openings in said base.

10. The combination of claim 1 wherein said bone staple is made of metal.

11. The combination of claim 10 wherein said retention element is made of metal.

12. A method for securing soft tissue to the bone structure of a patient comprising the steps of
(a) providing an assembly comprising
  (i) a bone implant comprising a transverse portion and a leg integral with and substantially perpendicular to said transverse portion, and
  (ii) a tissue retention element separable from said implant and comrising a base having an upper face and a lower face, means receiving said leg so that said retention element can slide upon said leg to a limiting position in which said upper face abuts said transverse portion, and a multiplicity of teeth distributed upon and extending from said lowr face;
(b) positioning said assembly so that said leg is directed toward said bone structure and said teeth are directed toward said soft tissue; and
(c) advancing said leg into said bone structure until said upper face of said base abuts said transverse portion of said implant and said teeth pierce said soft tissue, whereby said soft tissue is secured by said assembly to said bone structure.

* * * * *